United States Patent [19]

Fenyes et al.

[11] Patent Number: 4,778,813
[45] Date of Patent: Oct. 18, 1988

[54] POLYMERIC QUATERNARY AMMONIUM COMPOUNDS, THEIR PREPARATION AND USE

[75] Inventors: Joseph G. Fenyes, Germantown; John D. Pera, Memphis, both of Tenn.

[73] Assignee: Buckman Laboratories International, Inc., Memphis, Tenn.

[21] Appl. No.: 696,575

[22] Filed: Jan. 30, 1985

Related U.S. Application Data

[63] Continuation of Ser. No. 280,974, Jul. 7, 1981, abandoned.

[51] Int. Cl.$^4$ ............................................. A61K 31/435
[52] U.S. Cl. ...................... 514/357; 514/642; 514/643; 546/329; 564/286; 564/292; 210/735; 8/568; 8/606; 8/188; 162/32
[58] Field of Search ............... 364/281, 286, 392, 395; 564/292, 295, 281, 286; 514/357, 642, 643; 546/329; 210/735; 8/563, 606, 188; 162/32

[56] References Cited

U.S. PATENT DOCUMENTS

| 2,454,547 | 11/1948 | Bock et al. | 564/290 |
|---|---|---|---|
| 3,663,461 | 5/1972 | Witt | 564/290 |
| 3,974,220 | 8/1976 | Heib et al. | 564/290 |
| 4,012,446 | 3/1977 | Green et al. | 564/290 |
| 4,027,020 | 5/1977 | Green et al. | 564/290 |
| 4,036,959 | 7/1977 | Green et al. | 564/290 |
| 4,038,318 | 7/1977 | Tai | 564/290 |
| 4,091,113 | 5/1978 | Green et al. | 564/290 |
| 4,150,115 | 4/1979 | Jacquet et al. | 564/290 |
| 4,197,865 | 4/1980 | Jacquet et al. | 564/290 |
| 4,271,053 | 6/1981 | Kelsey et al. | 564/290 |
| 4,325,940 | 4/1982 | Green et al. | 564/290 |
| 4,374,244 | 2/1988 | Green et al. | 564/290 |

Primary Examiner—James H. Reamer
Attorney, Agent, or Firm—Finnegan, Henderson, Farabow, Garrett & Dunner

[57] ABSTRACT

Novel capped polymeric quaternary ammonium compositions formed by reacting ionene type polymers with tertiary amines are useful as microbicides, corrosion inhibitors, debonding agents, flocculants, softeners, and demulsifiers.

6 Claims, No Drawings

POLYMERIC QUATERNARY AMMONIUM COMPOUNDS, THEIR PREPARATION AND USE

This is a continuation of application Ser. No. 280,974, filed 7/7/81, now abandoned.

This invention relates to novel ionene type polymeric compositions, to the preparation of these polymers, and to their uses as microbicides, corrosion inhibitors, debonding agents in the manufacture of fluff pulp, flocculants in water and waste water treatment, softeners, anti-static agents, demulsifiers, and to improve dyeability and color fastness in textiles and paper.

The novel ionene polymeric compositions have the structure:

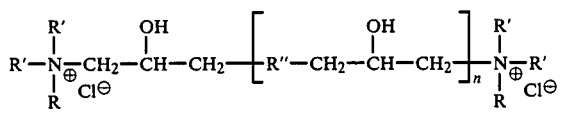

wherein R is methyl, ethyl, propyl, butyl, hydroxyethyl, or hydroxypropyl; characterized in that R and R' are identical when R is ethyl, propyl, butyl, hydroxyethyl or hydroxypropyl and when R is methyl, R' is independently methyl or an alkyl group containing 5 to 22 carbon atoms having 0 to 2 carbon to carbon double bonds, cyclohexyl, benzyl or phenyl; and characterized further in that R and R' may form a pyridyl group, R" is

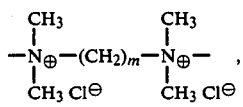

wherein m is an integer varying from 2 to 12,

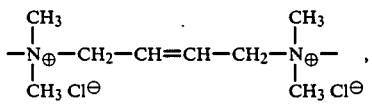

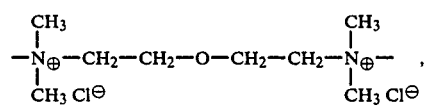

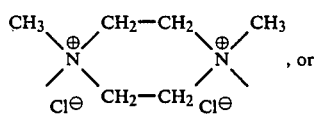

, or

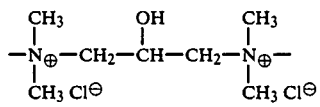

and n is an odd number from 1 to 201.

The polymers of this invention are prepared using a two-stage procedure. In the first stage X moles of N,N,N',N'-tetramethyl-N,N'-bis(3-chloro-2-hydroxypropyl)alkylanediammonium dichloride, N,N,N',N'-tetramethyl-N,N'-bis(3-chloro-2-hydroxypropyl)-2-butene-1,4-diammonium dichloride, N,N,N',N'-tetramethyl-N,N'-bis(3-chloro-2-hydroxypropyl)diethylether diammonium dichloride, N,N'-dimethyl-N,N'-bis(3-chloro-2-hydroxypropyl)piperazinium dichloride, or 1,3-bis[dimethyl-(3'-chloro-2'-hydroxypropylammonium chlorido)]-2-propanol is reacted at an elevated temperature in the presence of water with X-1 moles of a ditertiary amine. We have found suitable reaction temperature and times may vary from about 80° to 105° C. and from 1 to 30 hours. As used herein and in the appending claims, X is an integer varying from 2 to 101.

In the second stage, one mole of the precursor obtained in the first stage is reacted in the presence of water or a solvent with two moles of a monotertiary amine at a temperature varying from about 25° to 110° C. for a period varying from about 1 to 30 hours. Suitable solvents are water soluble lower alcohols and other polar compounds. The molecular weight of the precursor is calculated by multiplying X times the molecular weight of the chlorohydroxypropyl substituted ditertiary amine used and adding X−1 times the molecular weight of the second ditertiary amine.

The first stage of the process involves the reaction of an α,ω ditertiary amine with an α,ω dihalogenated alkyl compound. This reaction is known in the chemical literature as a Menschutkin Reaction and is used to prepare relatively low molecular weight polymers which are polymeric quaternary ammonium compounds known as ionene polymers. The molecular weights of these linear ionenes are generally about 50,000 or less.

The polymer chain length can be controlled by using the method of manufacture described in this invention. When two moles of the α,ω-dihalo compound (X moles) are reacted with one mole (X−1 mole) of the ditertiary amine, a very short polymer is formed. When the designation A is used for the dihalo compound and B for the ditertiary amine the polymer could then be designated A-B-A. When 5 moles of A and 4 moles of B are reacted the precursor then is A-B-A-B-A-B-A-B-A. The same general scheme can be used to a maximum of about 101 for A and 100 for B. Regardless of the number of moles of A and B used, there will be a halogen at either end of the precursor polymer. This precursor is then reacted with a monotertiary amine in the second stage to "cap" the ionene with additional quaternary ammonium groups. The nature of the tertiary amine and the length of the precursor polymer chain will determine the properties of the polymers of this invention and allow for the variation of hydrophilic and hydrophobic properties.

The N,N,N',N'-tetramethyl-N,N'-bis(3-chloro-2-hydroxypropyl)alkylanediammonium dichlorides used in the first stage are prepared by reacting the dihydrochloride salts of N,N,N',N'-tetramethyl-α,ω-alkanediamines wherein the alkane group contains 2 to 12 carbon aroms with two moles of epichlorohydrin. The other α,ω-dichlorodiquaternary ammonium chlorides are prepared in the same manner from the dihydrochloride salts of N,N,N',N'-tetramethyl-2-butene-1,4-diamine, 2,2'-oxybis(N,N-dimethylethanamine), 1,4-dimethylpiperazine, and N,N,N',N'-tetramethyl-2-hydroxy-1,3-propanediamine respectively. Each ditertiary amine used to produce the α,ω-dichlorodiquaternary ammonium compounds is then reacted as the free base with the α,ω-dichloro moieties to produce the ionene polymers of the first stage. In this invention it is not necessary that the same ditertiary amine be used in both reactants of the first stage. That is, the α,ω-dichloro derivative may be made with one ditertiary amine but reacted with another ditertiary amine or mixtures of ditertiary amines to produce the product of the first stage.

The monotertiary amines used in the second stage to cap the ionene polymers include aliphatic, alicyclic, alkylaromatic, aromatic and heterocyclic amines. The aliphatic groups may contain one or more carbon to carbon double bonds and may be substituted with hydroxyl groups. Examples of these amines are N,N-dimethylmethanamine (trimethylamine), N,N-diethylethanamine (triethylamine), N,N-dimethyl-1-octadecanamine (dimethylstearylamine), N,N-dimethyl-1-octadecenamine (dimethyloleylamine), N,N-dimethyl-1-decanamine (dimethylcaprylamine), N,N-dimethyl-1-dodecanamine (dimethyllaurylamine), N,N-dimethyl-1-tetradecanamine (dimethylmyristylamine), N,N-dimethyl-1-hexadecanamine (dimethylpalmitylamine), N-methyl-N-octadecyl-1-octadecanamine (methylditearylamine), N-decyl-N-methyl-1-decanamine (didecylmethylamine), methyldicocoamine, methyl di-hydrogenated tallow amine, 1-chloro-3-(dimethylamino)-2-propanol, N,N-dimethylbenzenamine (dimethylaniline), pyridine, N,N-dimethylbenzenemethanamine (dimethylbenzylamine), 2,2′,2″-nitrilotris ethanol (triethanolamine), 2-(dimethylamino)ethanol, 1,1′,1″-nitrilotris-2-propanol (triisopropanolamine), N,N-bis(1-methylethyl)-2-propanamine, and N,N-dimethylcyclohexylamine.

Polymeric compositions have been used in the past in the pulp and paper, textile and water treating industries for the uses described in this invention; but none, however, are entirely satisfactory. Some are useful as retention aids and flocculants but do not provide any of the other desired benefits. Ionene-type polymers which are prepared by reacting ditertiary amines with dihalo compounds are typically products with relatively low molecular weights. These products may be effective for controlling microorganisms, but their use as flooculants is limited. The most versatile cationic polymers as the polyethylenimines which can be manufactured in various molecular weight ranges by the selection of different catalysts and the use of cross-linking reagents. None of the polyethylenimines are good microbicides. In addition, the manufacture of polyethylenimines requires the use of the very toxic monomer ethylenimine which, in recent years, has been described as a carcinogen. Severe restrictions have been placed on the handling of this monomer in commercial and industrial plants by government regulatory agencies.

The degradative effect of microorganisms on organic materials is well known. Elimination or inhibition of growth of algae, bacteria, and fungi has been the objective of a large number of research projects and patents. Quaternary ammonium compounds and ionene polymers have found utility for the treatment of water used in various commercial and industrial cooling systems and in swimming pools. We have found that the cationic polymers of this invention are effective against algae, bacteria, and fungi in water systems even when used in very low concentrations.

The ionene polymers of this invention are soluble in water or other polar solvents such as alcohols, glycols and dimethylformamide. When used as flocculants, suitable quantities of the polymers of this invention may vary from as low as 0.1 ppm, based on the total weight of water and particulate matter, to as high as 25 ppm on the same basis with a preferred range of from 0.5 to 5 ppm. Concentrations which are suitable for control of microorganisms vary from 0.5 to 500 ppm based on the weight of the water being treated.

For control of corrosion in aqueous systems, concentrations of 0.5 to 500 ppm based on the weight of water treated are suitable with a preferred concentration range of 0.5 to 50 ppm. As a debonding agent for cellulose pulp, the ionene polymers of this invention are used in amounts varying from 0.1 to 2.0 parts per 100 parts of cellulose pulp fiber based on the dry weight of the fiber. The softening of textiles, paper or cellulose pulp sheets is achieved with these polymers in amounts of 0.1 to 1.0 parts per 100 parts of textile fabric, paper, or cellulose pulp based on the dry weight of material treated. As a demulsifier to break oil-in-water or water-in-oil emulsions, concentrations of 0.5 to 500 ppm based on the weight of the emulsion are suitable. When used as antistatic agents for textile fabrics, plastics, or paper, suitable quantities of the polymers of this invention may vary from 0.1 to 2.0 parts per 100 parts of material treated. To improve the dyeability and color fastness in textiles and paper, suitable polymer concentrations range from 0.05 to 1.0 part per 100 parts of dry textile fabric or dry paper.

It is, therefore, a principal object of our invention to provide novel ionene polymeric compositions.

It is another object of our invention to provide methods for controlling the growth of algae, bacteria, and fungi in aqueous sytems.

It is yet another object of this invention to provide a process for preparing the ionene polymeric compositions.

It is yet another object of our invention to provide methods of flocculating impurities in water and methods of improving processing of wastes.

It is yet another object of our invention to provide methods of improving dyeability and color fastness in textiles and of increasing the adhesion of water-proofing and flame-proofing finishes to fabrics.

These and other objects and advantages of the novel compositions and methods of this invention will become apparent as the description proceeds.

In order to disclose the nature of the present invention still more clearly, the following illustrative examples will be given. It is to be understood, however, that the invention is not to be limited to the specific conditions or details set forth in these examples except insofar as such limitations are specified in the appended claims.

EXAMPLE 1

Preparation of
N,N,N′,N′-tetramethyl-N,N′-bis(3-chloro-2-hydroxypropyl)ethylenediammonium dichloride (Precursor A)

A 1000 ml four-neck flask equipped with a reflux condenser, mechanical stirrer, thermometer and a dropping funnel was charged with 187.8 g (1.0 mole) of a 61.9 percent aqueous solution of N,N,N′,N′-tetramethyl-1,2-ethanediamine. The solution was cooled with an ice-water bath and 197.1 g (2 moles) of 37 percent hydrochloric acid was added at such a rate as to keep the temperature below 45° C. To the well-agitated N,N,N′,N′-tetramethyl-1,2-ethanediamine dihydrochloride solution so obtained, 185.0 g (2.0 moles) of epichlorohydrin was added slowly, taking care that the temperature did not exceed 45° C. After the addition was completed, the temperature was raised to between 60° and 70° C. for 30 minutes. A 65.7 percent aqueous solution of the title compound was obtained.

An aliquot of this aqueous solution was treated with four times its volume of acetone. A sticky precipitate formed and the liquid was decanted from it. The residue was dissolved in methanol and the resulting solution was diluted with acetone. The precipitate formed was filtered and dried over $P_2O_5$ under reduced pressure to give a very hygroscopic white solid.

EXAMPLES 2 to 14

Various quantities of the 65.7 percent aqueous solution of N,N,N',N'-tetramethyl-N,N'-bis(3-chloro-2-hydroxypropyl)ethylenediammonium dichloride (Precursor A) prepared in Example 1 and varying quantities of N,N,N',N'-tetramethyl-1,2-ethanediamine were refluxed for one hour while being stirred vigorously. The reaction products, polyquaternary ammonium salts, were obtained as aqueous solutions having total solids content as indicated in Table 1.

TABLE 1

| Example | Precursor Prepared | Precursor A to Diamine Mole ratio | Solids Content Percent |
| --- | --- | --- | --- |
| 2 | B | 2.0 to 1.0 | 65.8 |
| 3 | C | 3.0 to 2.0 | 65.8 |
| 4 | D | 4.0 to 3.0 | 65.8 |
| 5 | E | 5.0 to 4.0 | 66.9 |
| 6 | F | 6.0 to 5.0 | 66.9 |
| 7 | G | 7.0 to 6.0 | 66.9 |
| 8 | H | 8.0 to 7.0 | 66.9 |
| 9 | I | 16.0 to 15.0 | 50.0* |
| 10 | J | 26.0 to 25.0 | 50.0* |
| 11 | K | 38.0 to 37.0 | 50.0* |
| 12 | L | 51.0 to 50.0 | 50.0* |
| 13 | M | 76.0 to 75.0 | 50.0* |
| 14 | N | 101.0 to 100.0 | 50.0* |

*In these reactions, enough water was used to give products containing 50% solids.

Hygroscopic white solids were obtained when the aqueous solutions of the reaction products were treated with methanol and acetone using the procedure described in Example 1.

EXAMPLES 15 to 22

Various quantities of the 65.7 percent aqueous solution of Precursor A prepared in Example 1 were reacted at reflux temperature with a number of tertiary amines at a mole ratio of 2 to 1 of tertiary amine to Precursor A These reactions are included in Table 2.

TABLE 2

| Example | Tertiary Amine | Time of Reaction Hours | Solids Content Percent |
| --- | --- | --- | --- |
| 15 | N,N—dimethyl-1-dodecanamine | 4 | 80.5 |
| 16 | N,N—dimethyl-1-tetradecanamine | 4 | 81.7 |
| 17 | N,N—dimethyl-1-hexadecanamine | 4 | 84.5 |
| 18 | N,N—dimethyl-1-octadecanamine | 4 | 50.0* |
| 19 | 2,2',2''-nitrilo-trisethanol | 4 | 80.2 |
| 20 | N,N—diethylethanamine | 4 | 50.0* |
| 21 | 1,1',1''-nitrilotris-2-propanol | 4 | 50.0* |
| 22 | pyridine | 24 | 73.0 |

*In these reactions, enough water was used to obtain products containing 50% solids.

EXAMPLE 23

To a vigorously stirred refluxing solution of 50 g (0.12 mole) of Kemamine T-6501 (methyl dicocoamine, having an average molecular weight of 415.5 and supplied by Humko Sheffield Chemical) in 250 ml of acetone, 32.5 g (0.06 mole) of a 69.3 percent aqueous solution of the product of Example 1 was slowly added from a dropping funnel. After the introduction was completed, stirring and refluxing were continued for an additional 5 hours. The acetone solvent was distilled from the reaction mixture and the oily residue, containing 87.9 percent of the desired polyquaternary ammonium salt, was transferred to a container. On cooling, the product became a white, lard-like semisolid and had a limited water solubility.

EXAMPLE 24

To 40.0 g (0.0774 mole) of molten Kemamine T-9701 (methyl di-hydrogenated tallowamine having an average molecular weight of 516.8 and supplied by Humko Sheffield Chemical) maintained between 80° and 95° C., 20.9 g (0.0387 mole) of the Precursor A solution was slowly added while the reaction mixture was vigorously agitated. After stirring and heating for 16 hours, the reaction mixture was cooled and a polyquaternary ammonium salt was obtained as a white, lard-like semisolid containing 89.5 percent solids.

EXAMPLES 25 to 32

Various quantities of the 65.8 percent aqueous solution of Precursor B prepared in Example 2 were reacted at reflux temperature with a number of tertiary amines at a mole ratio of 2 to 1 of tertiary amine to Precursor B. These reactions are given in Table 3.

TABLE 3

| Example | Tertiary Amine | Time of Reaction Hours | Solids Content Percent |
| --- | --- | --- | --- |
| 25 | N,N—dimethyl-1-dodecanamine | 3 | 77.8 |
| 26 | N,N—dimethyl-1-tetradecanamine | 3 | 78.3 |
| 27 | N,N—dimethyl-1-hexadecanamine | 3 | 79.2 |
| 28 | N,N—dimethyl-1-octadecanamine | 5 | 25.0* |
| 29 | 2,2',2''-nitrilo-trisethanol | 5 | 75.7 |
| 30 | N,N—diethylethanamine | 30 | 50.0* |
| 31 | 1,1',1''-nitrilotris-2-propanol | 16 | 50.0* |
| 32 | pyridine | 24 | 73.1 |

*In these reactions, enough water was used to give products containing either 25% or 50% solids.

EXAMPLES 33 to 40

Various quantities of the 65.8 percent aqueous solution of Precursor C of Example 3 were treated at reflux temperature with a number of tertiary amines at a mole ratio of 2 to 1 of tertiary amine to Precursor C. These reactions are given in Table 4.

TABLE 4

| Example | Tertiary Amine | Time of Reaction Hours | Solids Content Percent |
| --- | --- | --- | --- |
| 33 | N,N—dimethyl-1-dodecanamine | 5 | 75.5 |

TABLE 4-continued

| Example | Tertiary Amine | Time of Reaction Hours | Solids Content Percent |
|---|---|---|---|
| 34 | N,N—dimethyl-1-tetradecanamine | 5 | 76.1 |
| 35 | N,N—dimethyl-1-hexadecanamine | 5 | 76.6 |
| 36 | N,N—dimethyl-1-octadecanamine | 5 | 25.0* |
| 37 | N,N—diethylethanamine | 24 | 50.0* |
| 38 | 2,2',2''-nitrilotrisethanol | 5 | 74.0 |
| 39 | pyridine | 24 | 72.2 |
| 40 | 1,1',1''-nitrilotris-2-propanol | 17 | 50.0* |

*In these reactions, enough water was used to give products containing either 25% or 50% solids.

EXAMPLES 41 to 74

In a manner analogous to Examples 33 to 40, solutions of Precursors D to N of Examples 4 to 14 were treated at reflux temperature with tertiary amines. The molar ratio of tertiary amine to Precursor was 2 to 1. The solvents used and the lengths of reaction times for these reactions are given in Table 5.

TABLE 5

| Example | Precursor | Tertiary Amine | Solvent | Time of Reaction Hours | Solids Content Percent |
|---|---|---|---|---|---|
| 41 | D | N,N—dimethyl-1-dodecanamine | water | 4 | 74.3 |
| 42 | D | N,N—dimethyl-1-tetradecanamine | water | 4 | 74.8 |
| 43 | D | N,N—dimethyl-1-hexadecanamine | water | 8 | 75.2 |
| 44 | D | N,N—dimethyl-1-octadecanamine | water/propylene glycol | 12 | 25.0** |
| 45 | D | 2,2',2''-nitrilotrisethanol | water | 5 | 73.1 |
| 46 | D | pyridine | water | 24 | 71.7 |
| 47 | D | N,N—diethylethanamine | water | 30 | 50.0* |
| 48 | D | 1,1',1''-nitrilotris-2-propanol | water | 18 | 50.0* |
| 49 | E | N,N—dimethyl-1-dodecanamine | water/propylene glycol | 4 | 25.0** |
| 50 | E | N,N—dimethyl-1-tetradecanamine | water | 4 | 25.0* |
| 51 | E | N,N—dimethyl-1-hexadecanamine | water/propylene glycol | 4 | 25.0** |
| 52 | E | N,N—dimethyl-1-octadecanamine | water/propylene glycol | 8 | 25.0** |
| 53 | F | N,N—dimethyl-1-dodecanamine | water/propylene glycol | 4 | 25.0** |
| 54 | F | N,N—dimethyl-1-tetradecanamine | water/propylene glycol | 4 | 25.0** |
| 55 | F | N,N—dimethyl-1-hexadecanamine | water/propylene glycol | 4 | 25.0** |
| 56 | F | N,N—dimethyl-1-octadecanamine | water/propylene glycol | 8 | 25.0** |
| 57 | G | N,N—dimethyl-1-dodecanamine | water/propylene glycol | 4 | 25.0** |
| 58 | G | N,N—dimethyl-1-tetradecanamine | water/propylene glycol | 4 | 25.0** |
| 59 | G | N,N—dimethyl-1-hexadecanamine | water/propylene glycol | 2 | 25.0** |
| 60 | G | N,N—dimethyl-1-octadecanamine | water/propylene glycol | 6 | 25.0** |
| 61 | H | N,N—dimethyl-1-dodecanamine | water | 4 | 25.0* |
| 62 | H | N,N—dimethyl-1-tetradecanamine | water/propylene glycol | 2 | 25.0** |
| 63 | H | N,N—dimethyl-1-hexadecanamine | water/propylene glycol | 2 | 25.0** |
| 64 | H | N,N—dimethyl-1-octadecanamine | water/propylene glycol | 6 | 25.0** |
| 65 | K | N,N—dimethyl-1-dodecanamine | water/isopropanol | 6 | 25.0*** |
| 66 | K | N,N—dimethyl-1-tetradecanamine | water | 6 | 25.0* |
| 67 | L | N,N—dimethyl-1-dodecanamine | water | 6 | 50.0* |
| 68 | L | N,N—dimethyl-1-tetradecanamine | water | 6 | 25.0* |
| 69 | M | N,N—dimethyl-1-dodecanamine | water | 6 | 50.0* |
| 70 | M | N,N—dimethyl-1-tetradecanamine | water/isopropanol | 6 | 25.0*** |

TABLE 5-continued

| Example | Precursor | Tertiary Amine | Solvent | Time of Reaction Hours | Solids Content Percent |
|---|---|---|---|---|---|
| 71 | N | N,N—dimethyl-1-dodecanamine | water | 6 | 50.0* |
| 72 | N | N,N—dimethyl-1-tetradecanamine | water/isopropanol | 6 | 25.0*** |
| 73 | N | N,N—dimethyl-1-hexadecanamine | water | 6 | 25.0* |
| 74 | N | N,N—dimethyl-1-octadecanamine | water/propylene glycol | 10 | 25.0** |

*In these reactions, enough water was used to give solutions containing the indicated amount of solids.
**In these reactions, a mixture of water and propylene glycol was used to give solutions containing the indicated amount of solids.
***In these reactions, a mixture of water and isopropanol was used for the dilution.

EXAMPLE 75

Preparation of N,N'-dimethyl-N,N'-bis(3-chloro-2-hydroxypropyl)-piperazinium dichloride (Precursor O)

A 5000 ml four-neck round-bottom flask equipped with a reflux condenser, mechanical stirrer, thermometer and a dropping funnel was charged with 1198.5 g (5.0 moles) of a 47.6 percent aqueous solution of 1,4-dimethylpiperazine. The solution was cooled by means of an ice-water bath and 985.5 g (10.0 moles) of 37 percent hydrochloric acid was added at such a rate as to keep the temperature below 45° C. To the well-agitated 1,4-dimethylpiperazine dihydrochloride solution so obtained, 925.2 g (10.0 moles) of epichlorohydrin was added slowly, again at such a rate as to keep the temperature below 45° C. After the addition was completed, the temperature of the reaction mixture was raised to between 60° and 70° C. for 30 minutes, followed by another hour at 100° C. A 59.8 percent solution of N,N'-dimethyl-N,N'-bis(3-chloro-2-hydroxypropyl) piperazinium dichloride was obtained.

EXAMPLES 76 to 78

Various quantities of the 59.8 aqueous solution of N,N'-dimethyl-N,N'-bis(3-chloro-2-hydroxypropyl)-piperazinium dichloride (Precursor O) prepared in Example 75 and varying quantities of 1,4-dimethylpiperazine were refluxed for 18 hours while being stirred vigorously. The reaction products, polyquaternary ammonium salts, were obtained as aqueous solutions having total solids content as indicated in Table 6.

TABLE 6

| Example | Precursor Prepared | Precursor O to 1,4-Dimethylpiperazine Moles Ratio | Solids Content Percent |
|---|---|---|---|
| 76 | P | 2 to 1 | 57.8 |
| 77 | Q | 3 to 2 | 57.3 |
| 78 | R | 4 to 3 | 57.1 |

EXAMPLES 79 to 85

Various quantities of the 59.8 percent aqueous solution of Precursor O of Example 75 were reacted with a number of tertiary amines at a mole ratio of 2 to 1 of tertiary amine to Precursor O. These reactions are given below in Table 7.

TABLE 7

| Example | Tertiary Amine | Time of Reaction Hours | Solids Content Percent |
|---|---|---|---|
| 79 | N,N—dimethyl-1-dodecanamine | 6 | 76.2 |
| 80 | N,N—dimethyl-1-tetradecanamine | 6 | 50.0* |
| 81 | N,N—dimethyl-1-hexadecanamine | 6 | 50.0* |
| 82 | N,N—dimethyl-1-octadecanamine | 8 | 25.0* |
| 83 | 2,2',2''-nitrilotrisethanol | 4 | 72.9 |
| 84 | pyridine | 18 | 66.0 |
| 85 | 1,1',1''-nitrilotris-2-propanol | 6 | 75.0 |

*In these reactions, enough water was used to give solutions containing either 25% or 50% of the product.

EXAMPLES 86 to 92

Various quantities of the 57.8 percent aqueous solution of Precursor P of Example 76 were reacted at reflux temperature with a number of tertiary amines at a mole ratio of 2 to 1 of tertiary amine to Precursor P. These reactions are given below in Table 8.

TABLE 8

| Example | Tertiary Amine | Time of Reaction Hours | Solids Content Percent |
|---|---|---|---|
| 86 | N,N—dimethyl-1-dodecanamine | 6 | 66.8 |
| 87 | N,N—dimethyl-1-tetradecanamine | 6 | 50.0* |
| 88 | N,N—dimethyl-1-hexadecanamine | 6 | 50.0* |
| 89 | N,N—dimethyl-1-octadecanamine | 10 | 25.0** |
| 90 | 2,2',2''-nitrilotrisethanol | 4 | 64.4 |
| 91 | pyridine | 18 | 68.5 |
| 92 | 1,1',1''-nitrilotris-2-propanol | 6 | 66.5 |

*In these reactions, enough water was used to give products containing 50.0% solids.
**In this reaction, enough propylene glycol was used to give products containing 25.0% solids.

EXAMPLES 93 to 99

Various quantities of the 57.3 percent aqueous solutions of Precursor Q of Example 77 were treated at reflux temperature with a number of tertiary amines at a mole ratio of 2 to 1 of tertiary amine to Precursor Q. These reactions are included in Table 9.

TABLE 9

| Example | Tertiary Amine | Time of Reaction Hours | Solids Content Percent |
|---|---|---|---|
| 93 | N,N—dimethyl-1-dodecanamine | 6 | 53.9 |
| 94 | N,N—dimethyl-1-tetradecanamine | 6 | 64.6 |
| 95 | N,N—dimethyl-1-hexadecanamine | 6 | 65.3 |
| 96 | N,N—dimethyl-1-octadecanamine | 10 | 25.0* |
| 97 | 2,2',2''-nitrilotrisethanol | 4 | 65.3 |
| 98 | pyridine | 18 | 59.8 |
| 99 | 1,1',1''-nitrilotris-2-propanol | 6 | 63.3 |

*In this reaction, enough propylene glycol was used to give a product containing 25.0% solids.

EXAMPLES 100 to 106

Various quantities of the 57.1 percent aqueous solution of Precursor R of Example 78 were treated at reflux temperature with a number of tertiary amines at a mole ratio of 2 to 1 of tertiary amine to Precursor R. These reactions are included in Table 10.

TABLE 10

| Example | Tertiary Amine | Time of Reaction Hours | Solids Content Percent |
|---|---|---|---|
| 100 | N,N—dimethyl-1-dodecanamine | 6 | 62.9 |
| 101 | N,N—dimethyl-1-tetradecanamine | 6 | 62.7 |
| 102 | N,N—dimethyl-1-hexadecanamine | 6 | 63.3 |
| 103 | N,N—dimethyl-1-octadecanamine | 10 | 25.0* |
| 104 | 2,2',2''-nitrilotrisethanol | 4 | 60.7 |
| 105 | pyridine | 18 | 59.0 |
| 106 | 1,1',1''-nitrilotris-2-propanol | 6 | 61.7 |

*In this reaction, enough propylene glycol was used to give a product containing 25.0% solids.

EXAMPLE 107

Preparation of N,N,N',N'-tetramethyl-N,N'-bis(3-chloro-2-hydroxypropyl)-2-butene-1,4-diammonium dichloride (Precursor S)

A 2000 mL four-neck, round-bottom flask equipped with a reflux condenser, a mechanical stirrer, thermometer and a dropping funnel was charged with 142.2 g (1.0 mole) of N,N,N',N'-tetramethyl-2-butene-1,4-diamine and 276.1 g water. The stirred mixture was cooled by means of an ice-water bath and 197.1 g (2.0 moles) of 37 percent hydrochloric acid was added at such a rate as to keep the temperature below 45° C. To the well-agitated N,N,N',N'-tetramethyl-2-butene-1,4-diamine dihydrochloride solution, 185.0 g (2.0 moles) of epichlorohydrin was added slowly, again at such a rate as to keep the temperature below 45° C. After the addition was completed, the reaction mixture was refluxed 4 hours to produce an aqueous solution containing 50 percent of N,N,N',N'-tetramethyl-N,N'-bis(3-chloro-2-hydroxypropyl)-2-butene-1,4-diammonium dichloride.

EXAMPLES 108 to 110

Various quantities of the 50.0 percent aqueous solution of N,N,N',N'-tetramethyl-N,N'-bis(3-chloro-2-hydroxypropyl)-2-butene-1,4-diammonium dichloride (Precursor S) prepared in Example 107 and varying quantities of 1,4-bis(dimethylamino)-2-butene were refluxed for 4 hours while being stirred vigorously. The reaction products, polyquaternary ammonium salts, were obtained as 50.0 percent aqueous solutions. These reactions are included in Table 11.

TABLE 11

| Example | Precursor Prepared | Precursor S to Diamine Mole Ratio | Water Added |
|---|---|---|---|
| 108 | T | 2.0 to 1.0 | as needed |
| 109 | U | 3.0 to 2.0 | as needed |
| 110 | V | 4.0 to 3.0 | as needed |

EXAMPLES 111 to 117

Various quantities of the 50.0 percent aqueous solution of Precursor S prepared in Example 107 were reacted at reflux temperature with a number of tertiary amines at a mole ratio of 2 to 1 of tertiary amine to Precursor S. These reactions are included in Table 12.

TABLE 12

| Example | Tertiary Amine | Time of Reaction Hours | Solids Content Percent |
|---|---|---|---|
| 111 | N,N—dimethyl-1-dodecanamine | 5 | 67.3 |
| 112 | N,N—dimethyl-1-tetradecanamine | 5 | 68.8 |
| 113 | N,N—dimethyl-1-hexadecanamine | 5 | 70.1 |
| 114 | N,N—dimethyl-1-octadecanamine | 6 | 25.0* |
| 115 | pyridine | 18 | 58.2 |
| 116 | 2,2',2''-nitrilotrisethanol | 6 | 63.6 |
| 117 | 1,1',1''-nitrilotris-2-propanol | 6 | 66.1 |

*In this reaction, enough propylene glycol was used to give a product containing 25.0% solids.

EXAMPLES 118 to 124

Various quantities of the 50.0 percent aqueous solution of Precursor T prepared in Example 108 were reacted at reflux temperature with a number of tertiary amines at a mole ratio of 2 to 1 of tertiary amine to Precursor T. These reactions are given in Table 13.

TABLE 13

| Example | Tertiary Amine | Time of Reaction Hours | Solids Content Percent |
|---|---|---|---|
| 118 | N,N—dimethyl-1-dodecanamine | 6 | 50.0* |
| 119 | N,N—dimethyl-1-tetradecanamine | 6 | 50.0* |
| 120 | N,N—dimethyl-1-hexadecanamine | 6 | 50.0* |
| 121 | N,N—dimethyl-1-octadecanamine | 6 | 25.0** |
| 122 | pyridine | 18 | 54.8 |
| 123 | 2,2',2''-nitrilotrisethanol | 6 | 56.8 |
| 124 | 1,1',1''-nitrilotris- | 6 | 58.4 |

TABLE 13-continued

| Example | Tertiary Amine | Time of Reaction Hours | Solids Content Percent |
|---|---|---|---|
| | 2-propanol | | |

*In these reactions, enough water was used to give products containing 50.0% solids.
**In this reaction, enough propylene glycol was used to give a product containing 25.0% solids.

EXAMPLES 125 to 131

Various quantities of the 50.0 percent aqueous solution of Precursor U prepared in Example 109 were reacted at reflux temperature with a number of tertiary amines at a mole ratio of 2 to 1 of tertiary amine to Precursor U. These reactions are included in Table 14.

TABLE 14

| Example | Tertiary Amine | Time of Reaction Hours | Solids Content Percent |
|---|---|---|---|
| 125 | N,N—dimethyl-1-dodecanamine | 6 | 50.0* |
| 126 | N,N—dimethyl-1-tetradecanamine | 6 | 50.0* |
| 127 | N,N—dimethyl-1-hexadecanamine | 6 | 50.0* |
| 128 | N,N—dimethyl-1-octadecanamine | 6 | 25.0** |
| 129 | pyridine | 18 | 52.5 |
| 130 | 2,2',2''-nitrilotrisethanol | 6 | 54.5 |
| 131 | 1,1',1''-nitrilotris-2-propanol | 6 | 55.7 |

*In these reactions, enough water was used to give products containing 50.0% solids.
**In this reaction, enough propylene glycol was used to give a product containing 25.0% solids.

EXAMPLES 132 to 138

Various quantities of the 50.0 percent aqueous solution of Precursor V prepared in Example 100 were reacted at reflux temperature with a number of tertiary amines at a mole ratio of 2 to 1 of the tertiary amine to Precursor V. These reactions are included in Table 15.

TABLE 15

| Example | Tertiary Amine | Time of Reaction Hours | Solids Content Percent |
|---|---|---|---|
| 132 | N,N—dimethyl-1-dodecanamine | 6 | 50.0* |
| 133 | N,N—dimethyl-1-tetradecanamine | 6 | 50.0* |
| 134 | N,N—dimethyl-1-hexadecanamine | 6 | 50.0* |
| 135 | N,N—dimethyl-1-octadecanamine | 6 | 25.0** |
| 136 | pyridine | 18 | 51.9 |
| 137 | 2,2',2''-nitrilotrisethanol | 6 | 53.4 |
| 138 | 1,1',1''-nitrilotris-2-propanol | 6 | 54.3 |

*In these reactions, enough water was used to give products containing 50.0% solids.
**In this reaction, enough propylene glycol was used to give a product containing 25.0% solids.

EXAMPLE 139

Preparation of N,N,N',N'-tetramethyl-N,N'-bis(3-chloro-2-hydroxypropyl)diethylether diammonium dichloride (Precursor W)

A 2000 mL four-neck round-bottom flask equipped with a reflux condenser, a merchanical stirrer, thermometer and dropping funnel was charged with 160.2 g (1.0 mole) of 2,2'-oxybis(N,N-dimethylethanamine) and 293.9 g water. The vigorously agitated mixture was cooled by means of an ice-water bath while 197.1 g (2.0 moles) of 37 percent hydrochloric acid was introduced at such a rate as to keep the temperature of the reaction mixture below 45° C. The 2,2'-oxybis(N,N-dimethylethanamine)dihydrochloride thus prepared was treated with 185.0 g (2.0 moles) of epichlorohydrin while agitation was maintained and care was taken to keep the temperature below 45° C. After the addition was completed, the reaction mixture was refluxed 6 hours. A 50 percent aqueous solution of the title compound was obtained.

EXAMPLES 140 to 142

Various quantities of the 50.0 percent aqueous solution of N,N,N',N'-tetramethyl-N,N'-bis(3-chloro-2-hydroxypropyl)diethylether diammonium dichloride (Precursor W) prepared in Example 139 and varying quantities of 2,2'-oxybis(N,N-dimethylethanamine) were refluxed for 6 hours while being stirred vigorously. The reaction products, polyquaternary ammonium salts, were obtained as aqueous solutions having total solids contents as indicated in Table 16.

TABLE 16

| Example | Precursor Prepared | Precursor W to Diamine Mole Ratio | Solids Content Percent |
|---|---|---|---|
| 140 | X | 2 to 1 | 50.0* |
| 141 | Y | 3 to 2 | 50.0* |
| 142 | Z | 4 to 3 | 50.0* |

*Enough water was used to give products containing 50.0% solids.

EXAMPLES 143 to 149

Varioius quantities of the 50.0 percent aqueous solution of Precursor W prepared in Example 139 were reacted at reflux temperature with a number of tertiary amines at a mole ratio of 2 to 1 of tertiary amine to Precursor W. These reactions are included in Table 17.

TABLE 17

| Example | Tertiary Amine | Time of Reaction Hours | Solids Content Percent |
|---|---|---|---|
| 143 | N,N—dimethyl-1-dodecanamine | 6 | 66.9 |
| 144 | N,N—dimethyl-1-tetradecanamine | 6 | 68.3 |
| 145 | N,N—dimethyl-1-hexadecanamine | 6 | 69.6 |
| 146 | N,N—dimethyl-1-octadecanamine | 6 | 25.0* |
| 147 | pyridine | 18 | 68.0 |
| 148 | 2,2',2''-nitrilotrisethanol | 4 | 63.1 |
| 149 | 1,1',1''-nitrilotris-2-propanol | 4 | 65.7 |

*In this reaction, enough propylene glycol was used to give a product containing 25.0% solids.

EXAMPLES 150 to 156

Various quantities of the 50.0 percent aqueous solution of Precursor X prepared in Example 140 were reacted at reflux temperature with a number of tertiary amines at a mole ratio of 2 to 1 of tertiary amine to Precursor X. These reactions are given in Table 18.

TABLE 18

| Example | Tertiary Amine | Time of Reaction Hours | Solids Content Percent |
| --- | --- | --- | --- |
| 150 | N,N—dimethyl-1-dodecanamine | 6 | 58.8 |
| 151 | N,N—dimethyl-1-tetradecanamine | 6 | 59.7 |
| 152 | N,N—dimethyl-1-hexadecanamine | 6 | 60.6 |
| 153 | N,N—dimethyl-1-octadecanamine | 6 | 25.0* |
| 154 | pyridine | 18 | 53.7 |
| 155 | 2,2',2''-nitrilotrisethanol | 4 | 56.5 |
| 156 | 1,1',1''-nitrilotris-2-propanol | 4 | 58.0 |

*In this reaction, enough propylene glycol was used to give a product containing 25.0% solids.

EXAMPLES 157 to 163

Various quantities of the 50.0 percent aqueous solution of Precursor Y prepared in Example 141 were reacted at reflux temperature with a number of tertiary amines at a molar ratio of 2 to 1 of tertiary amine to Precursor Y. These reactions are given in Table 19.

TABLE 19

| Example | Tertiary Amine | Time of Reaction Hours | Solids Content Percent |
| --- | --- | --- | --- |
| 157 | N,N—dimethyl-1-dodecanamine | 6 | 55.9 |
| 158 | N,N—dimethyl-1-tetradecanamine | 6 | 56.6 |
| 159 | N,N—dimethyl-1-hexadecanamine | 6 | 57.3 |
| 160 | N,N—dimethyl-1-octadecanamine | 6 | 25.0* |
| 161 | pyridine | 18 | 52.4 |
| 162 | 2,2',2''-nitrilotrisethanol | 4 | 54.3 |
| 163 | 1,1',1''-nitrilotris-2-propanol | 4 | 55.4 |

*In this reaction, enough propylene glycol was used to give a product containing 25.0% solids.

EXAMPLES 164 to 170

Various quantities of the 50.0 percent aqueous solution of Precursor Z prepared in Example 142 were reacted at reflux temperature with a number of tertiary amines at a molar ratio of 2 to 1 of tertiary amine to Precursor Z. These reactions are given in Table 20.

TABLE 20

| Example | Tertiary Amine | Time of Reaction Hours | Solids Content Percent |
| --- | --- | --- | --- |
| 164 | N,N—dimethyl-1-dodecanamine | 6 | 54.5 |
| 165 | N,N—dimethyl-1-tetradecanamine | 6 | 55.0 |
| 166 | N,N—dimethyl-1-hexadecanamine | 6 | 55.5 |
| 167 | N,N—dimethyl-1-octadecanamine | 6 | 25.0* |
| 168 | pyridine | 18 | 51.8 |
| 169 | 2,2',2''-nitrilotrisethanol | 4 | 53.2 |
| 170 | 1,1',1''-nitrilotris-2-propanol | 4 | 54.0 |

*In this reaction, enough propylene glycol was used to give a product containing 25.0% solids.

EXAMPLE 171

Preparation of 1,3-bis[dimethyl-(3'-chloro-2'-hydroxypropylammonium chlorido)]-2-propanol (Precursor AA)

A 1000 mL four-neck flask equipped with a reflux condenser, mechanical stirrer, thermometer and a dropping funnel was charged with 149.5 g (1.0 mole) of a 98 percent, N,N,N',N'-tetramethyl-2-hydroxy-1,3-propanediamine. The flask was immersed into an ice-water bath while 197.2 g (2.0 moles) of concentrated hydrochloric acid was introduced at such a rate as to keep the temperature between 35° and 45° C. To the N,N,N',N'-tetramethyl-2-hydroxy-1,3-propanediamine dihydrochloride so obtained, 185.0 g (2.0 moles) of epichlorohydrin was added slowly, taking care that the temperature did not exceed 45° C. After the addition was completed, the temperature was raised to between 60° and 71° C. for 30 minutes. A 77.2 percent solution of the title compound was obtained.

EXAMPLES 172 to 181

Various quantities of the 77.2 percent aqueous solution of 1,3-bis[dimethyl-(3'-chloro-2'-hydroxypropylammonium chlorido)]-2-propanol (Precursor AA) prepared in Example 171 and varying quantities of N,N,N',N'-tetramethyl-2-hydroxy-1,3-propanediamine were refluxed for 4 hours while being stirred vigorously. The reaction products, polyquaternary ammonium salts, were obtained as aqueous solutions having total solids content as indicated in Table 21.

TABLE 21

| Example | Precursor Prepared | Precursor AA to Diamine Mole Ratio | Solids Content Percent |
| --- | --- | --- | --- |
| 172 | BB | 2 to 1 | 79.7 |
| 173 | CC | 3 to 2 | 80.5 |
| 174 | DD | 4 to 3 | 80.9 |
| 175 | EE | 5 to 4 | 81.0 |
| 176 | FF | 26 to 25 | 81.7 |
| 177 | GG | 51 to 50 | 81.7 |
| 178 | HH | 101 to 100 | 81.8 |
| 179 | II | 201 to 200 | 81.8 |
| 180 | JJ | 251 to 250 | 81.8 |
| 181 | KK | 1 to 1 | 81.8 |

EXAMPLES 182 to 186

Various quantities of the 77.2 percent aqueous solution of Precursor AA prepared in Example 171 were treated at reflux temperature with a number of tertiary amines at a mole ratio of 2 to 1 tertiary amine to Precursor AA. These reactions are given in Table 22.

TABLE 22

| Example | Tertiary Amine | Time of Reaction Hours | Solids Content Percent |
|---|---|---|---|
| 182 | N,N—dimethyl-1-decanamine | 4 | 50.0* |
| 183 | N,N—dimethyl-1-dodecanamine | 4 | 50.0* |
| 184 | N,N—dimethyl-1-tetradecanamine | 4 | 50.0* |
| 185 | N,N—dimethyl-1-hexadecanamine | 4 | 50.0* |
| 186 | N,N—dimethyl-1-octadecanamine | 4 | 50.0* |

*In these reactions, enough water was used to obtain products containing 50.0% solids.

EXAMPLE 187

The effect of the novel ionene type polymeric compositions described in the preceding examples on the percentage kill of the bacterium *Enterobacter aerogenes* was determined using the method described in U.S. Pat. No. 2,881,070 with the modification described in U.S. Pat. No. 4,054,542. The results are included in Table 23.

TABLE 23

| Ionene polymer from examples | Concentration in parts per million required for 80 percent kill or greater of *Enterobacter aerogenes* in a basal salt substrate after 18 hours contact | | |
|---|---|---|---|
| | pH 6.0-6.5 | pH 7.0-7.5 | pH 8.0-8.5 |
| 2 | 2.0 | 2.0-4.0 | 4.0 |
| 3 | 1.0 | 0.5 | 4.0 |
| 4 | 1.0 | 0.5 | 2.0 |
| 15 | 0.1 | 0.1 | 0.1 |
| 16 | — | 2.0 | 2.0 |
| 20 | 4.0 | 2.0 | 1.0 |
| 21 | 1.0 | 0.5 | 1.0 |
| 22 | — | — | 0.5 |
| 25 | 1.0 | 0.5 | 0.5 |
| 26 | 1.0 | 1.0 | 0.5 |
| 27 | 0.5 | 2.0 | 0.5 |
| 30 | 4.0 | 4.0 | >4.0 |
| 31 | 2.0-4.0 | 1.0 | 2.0 |
| 32 | 1.0 | 0.5 | 2.0 |
| 33 | 0.5-1.0 | 0.5-1.0 | 1.0 |
| 34 | 1.0 | 0.5-1.0 | 1.0 |
| 35 | 1.0 | 1.0 | 0.5 |
| 37 | 2.0 | 1.0 | 1.0 |
| 38 | 0.5-1.0 | 0.5 | 0.5-1.0 |
| 39 | 1.0 | 0.5 | 0.5-1.0 |
| 42 | 2.0-4.0 | 2.0 | >4.0 |
| 43 | 1.0 | 0.5 | 1.0 |
| 45 | 1.0-2.0 | 1.0-2.0 | 2.0 |
| 46 | — | 1.0 | 4.0 |
| 47 | 4.0 | 2.0 | 4.0 |
| 48 | 2.0 | 0.5-1.0 | 2.0 |
| 75 | 1.0 | — | — |
| 76 | — | 4.0 | >4.0 |
| 78 | — | 2.0 | 4.0 |
| 79 | 4.0 | 4.0 | — |
| 80 | 4.0 | 4.0 | — |
| 81 | 4.0 | 4.0 | — |
| 86 | 2.0 | 2.0 | 2.0 |
| 87 | 2.0 | 2.0 | 2.0 |
| 88 | 2.0 | 2.0 | 2.0 |
| 93 | — | 1.0-2.0 | 0.5 |
| 94 | — | 1.0-2.0 | 0.5 |
| 95 | — | 1.0-2.0 | 0.5 |
| 100 | 2.0 | 1.0-2.0 | 2.0 |
| 101 | 2.0 | 1.0-2.0 | 2.0 |
| 102 | 2.0 | 1.0-2.0 | 2.0 |
| 107 | — | — | >4.0 |
| 111 | 1.0 | 2.0 | 2.0 |
| 112 | 1.0 | 2.0 | 2.0 |
| 115 | 2.0 | 2.0 | 0.5 |

EXAMPLE 188

The effect of some of the ionene type polymeric compositions described in the preceding Examples on the inhibition of the fungi *Chaetomium globosum* and *Penicillium roqueforti* was determined using the method described in U.S. Pat. No. 3,356,706 with the modification described in U.S. Pat. No. 4,054,542. The compositions described in Examples 3, 15, 16, 17, 25, 26 and 27 completely prevented the growth of both fungi at 8 parts per million and the compositions of Examples 37, 38 and 39 prevented the growth of *Chaetomium globosum* alone at 8 parts per million.

EXAMPLES 189

The effect of some of the ionene type polymeric compositions described in the preceding examples of the inhibition of algae *Chlorella pyrenoidosa*, *Chlorococcum hypnosporum*, and *Phormidium inundatum* was determined using the procedure described in Example 2 of U.S. Pat. No. 3,771,989. The results are included in Table 24. Observations of growth were made after 28 days on the basis of the following Key:
4=Excellent
3=Good
2=Poor
1=Very poor, scant, questionable
0=No growth

TABLE 24

| Ionene polymer from examples | Concentration in parts per million required for inhibition of growth after 28 days | | |
|---|---|---|---|
| | *Chlorella pyrenoidosa* | *Chlorococcum hypnosporum* | *Phormidium inundatum* |
| 2 | 4.0 | 2.0-4.0 | >8.0 |
| 3 | 1.0 | 2.0 | >1.0 |
| 4 | 4.0 | 2.0 | 8.0 |
| 15 | 2.0 | 2.0 | 2.0 |
| 16 | 2.0 | 2.0 | 2.0 |
| 17 | 2.0 | 2.0 | 2.0 |
| 23 | 8.0 | 4.0 | — |
| 25 | 1.0-2.0 | 1.0 | 2.0 |
| 26 | 2.0 | 1.0 | 2.0 |
| 27 | 2.0 | 1.0 | 2.0 |
| 30 | 8.0 | 8.0 | >8.0 |
| 31 | 4.0 | 4.0 | >4.0 |
| 32 | 4.0 | 4.0 | >4.0 |
| 42 | 4.0 | 4.0 | 4.0 |
| 43 | 2.0 | 8.0 | 8.0 |
| 45 | 8.0 | 4.0 | — |
| 76 | 8.0 | 8.0 | — |
| 77 | 4.0 | 4.0-8.0 | — |
| 78 | 1.0-2.0 | — | — |
| 79 | 2.0 | 2.0 | 4.0 |
| 80 | 2.0 | 4.0 | — |
| 81 | 2.0 | 4.0 | 4.0 |
| 86 | 2.0-4.0 | 4.0 | — |
| 87 | 2.0-4.0 | 4.0 | — |
| 88 | 2.0-4.0 | 4.0 | 8.0 |
| 93 | 2.0 | 2.0 | 8.0 |
| 94 | 2.0 | 2.0 | 8.0 |
| 95 | 2.0 | 2.0 | 8.0 |
| 111 | 1.0 | 1.0 | 2.0 |
| 112 | 1.0 | 1.0 | 2.0 |
| 113 | 1.0 | 1.0 | 2.0 |

TABLE 24-continued

| Ionene polymer from examples | Concentration in parts per million required for inhibition of growth after 28 days | | |
|---|---|---|---|
| | *Chlorella pyrenoidosa* | *Chlorococcum hypnosporum* | *Phormidium inundatum* |
| 115 | 8.0 | 8.0 | >8.0 |

EXAMPLE 190

The flocculating properties of the ionene type polymers of this invention were determined using a suspension of kaolin clay in water. The procedure was as follows:

A 2-liter jar was charged with 1350 mL of water and 150 mL of a slurry containing 6.0 grams of kaolin clay. The clay had been dispersed by agitating stock solution with a Waring blender. A paddle turning at 100 rpm was then inserted into the beaker and a solution of the ionene polymer to be tested was added. The mixture was agitated for one minute. The settling rate of the clay and the clarity of the supernatant was observed.

The flocculatory properties of the ionene-type polymers were graded on a scale of 0 to 10 (10 is perfect). Several compounds listed in the foregoing example were tested. The results are included in Table 25.

TABLE 25

| Example | Concentration of polymer parts per million | Flocculation |
|---|---|---|
| Control | 0 | 0 |
| 181 | 3.3 | 3 |
| 182 | 3.3 | 3 |
| 183 | 3.3 | 3 |
| 184 | 3.3 | 8 |
| 185 | 3.3 | 9 |

EXAMPLE 191

The ionene-type polymers of this invention were used in the treatment of wet bleached pine kraft pulp in the form of an aqueous slurry with a pulp consistency of 0.5 percent. Handsheets were formed from the pulp on a laboratory handsheet machine to produce 20 cm×20 cm pulp sheets with basis weights of 120 g/m². After the sheets were formed, pressed and dried by the standard procedure, the debonding effect was evaluated by determining the fiber-to-fiber internal bonding strength of these sheets by means of a Scott Internal Bond Tester as described in TAPPI UM-403. The debonding effect was expressed as a percentage factor calculated as follows:

Internal Bond Factor =

$$\frac{\text{(Internal Bond of Treated Pulp Sheet)} \times 100}{\text{Internal Bond of Untreated Pulp Sheet}}$$

Thus, the untreated pulp would have an Internal Bond Factor of 100 and debonded pulp would have an Internal Bond Factor below 100; the lower this factor, the greater the degree of debonding achieved.

Table 26 shows the results obtained with the ionene polymers when they were evaluated by the indicated test method. Treatment rates are in weight percent based on the dry weight of pulp.

TABLE 26

| Example | Treatment Rate Percent | Internal Bond Factor |
|---|---|---|
| 15 | 0.5 | 70 |
| 16 | 0.5 | 63 |
| 18 | 0.5 | 81 |
| 23 | 0.5 | 48 |
| 85 | 0.5 | 82 |
| 86 | 0.5 | 78 |

These results show that the ionene polymers of this invention are good debonding agents, reducing the internal bond strength to as low as 48 percent of the strength of the original untreated pulp.

The invention having thus been described, what is claimed and desired to be secured by Letters Patent is:

1. A polymeric quaternary ammonium composition having the structure

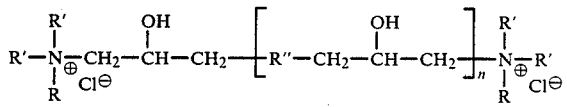

wherein R is methyl, ethyl, propyl, butyl, hydroxyethyl or hydroxypropyl; characterized in that R and R' are identical when R is ethyl, propyl, butyl, hydroxyethyl or hydroxypropyl and when R is methyl, R' is independently methyl, an alkyl group containing 5 to 22 carbon atoms having 0 to 2 carbon to carbon double bonds, cyclohexyl, benzyl or phenyl; and characterized further in that R and R' may form a pyridyl group; R'' is

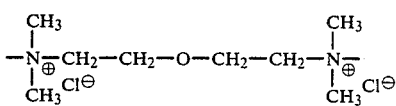

and n is an odd number from 1 to 201.

2. The method of preparing the polymeric quaternary ammonium composition of claim 1 which comprises reacting X moles of N,N,N',N'-tetramethyl-N,N'-bis(3-chloro-2-hydroxypropyl)diethylether diammonium dichloride in the presence of water at 80° to 105° C. from 1 to 30 hours with X−1 moles of a ditertiary amine to form a precursor which is subsequently reacted in water or a polar organic solvent with two moles of a monotertiary amine per mole of precursor at a temperature of 25° to 110° C. for 1 to 30 hours wherein X varies from 2 to 101.

3. A method of flocculating solids from an aqueous system containing suspended or dissolved solids, which comprises adding to said aqueous system a flocculant comprising 1 or more of the polymeric quaternary ammonium compounds of claim 1 in an amount sufficient to cause the flocculation of said solids.

4. A method of improving the retention of dyes, water-proofing and flame-proofing materials in textiles during the finishing of textiles, which comprises adding to the finishing system one or more of the polymeric quaternary ammonium compositions of claim 1 in an amount sufficient to achieve the desired increase in retention.

5. A method of inhibiting the growth and proliferation of microorganisms selected from the group consisting of algae, bacteria, and fungi which comprises contacting said microorganisms with a polymeric quaternary ammonium composition of claim 1 in an amount sufficient to inhibit the growth and proliferation of said microorganisms.

6. A method for treating cellulose pulp to reduce inter-fiber bonding, thus imparting a low degree of mechanical strength to webs formed therefrom, which comprises adding to the cellulose pulp fiber slurry prior to or during the formation of the slurry into a web, a polymeric quaternary ammonium composition of claim 1 in an amount sufficient to achieve the desired decrease in inter-fiber bonding.

* * * * *